United States Patent [19]
Asako et al.

[11] 3,937,699
[45] Feb. 10, 1976

[54] 6-(1'-CYCLOHEXENYLGLYCINAMIDO)-PENICILLANIC ACID AND SALTS THEREOF

[75] Inventors: Tsunehiko Asako, Kyoto; Takenobu Soma, Suita; Hirotomo Masuya, Kobe; Tadatsugu Harukawa, Kyoto; Takuichi Miki, Amagasaki, all of Japan

[73] Assignee: Takeda Chemical Industries, Ltd., Osaka, Japan

[22] Filed: May 7, 1974

[21] Appl. No.: 467,823

Related U.S. Application Data
[62] Division of Ser. No. 188,622, Oct. 12, 1971, Pat. No. 3,824,237.

[30] Foreign Application Priority Data

| Oct. 12, 1970 | Japan | 45-89918 |
| May 24, 1971 | Japan | 46-35382 |
| Aug. 3, 1971 | Japan | 46-58905 |
| Aug. 28, 1971 | Japan | 46-66104 |

[52] U.S. Cl. ................ 260/239.1; 260/306.7 C
[51] Int. Cl.$^2$ .............................. C07D 499/46
[58] Field of Search .......................... 260/239.1

[56] References Cited
UNITED STATES PATENTS

| 2,985,648 | 12/1961 | Doyle et al. ........... 260/239.1 |
| 3,120,514 | 12/1964 | Doyle et al. ........... 260/239.1 |
| 3,485,819 | 1/1970 | Weisenborn ........... 260/239.1 |
| 3,673,183 | 1/1972 | Erickson ............... 260/243 C |
| 3,741,960 | 3/1973 | Alburn et al. .......... 260/239.1 |

*Primary Examiner*—Gerald A. Schwartz
*Attorney, Agent, or Firm*—Wenderoth, Lind & Ponack

[57] ABSTRACT

6-(1'-cyclohexenylglycinamido)penicillanic acid and salts thereof, which have both a broad spectrum antibacterial action and strong activity against *Escherichia coli*.

2 Claims, No Drawings

6-(1'-CYCLOHEXENYLGLYCINAMIDO)PENICIL-LANIC ACID AND SALTS THEREOF

This is a division, of application Ser. No. 188,622, filed Oct. 12, 1971. now U.S. Pat. No. 3,824,237.

The present invention relates to novel and useful antibacterial compounds and methods for producing them, and more particularly to compounds represented by the general formula:

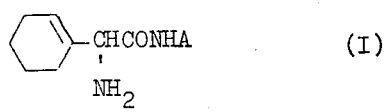

[wherein A is a group which forms 6-aminopenicillanic acid (hereinafter referred to briefly as 6-APA), 7-aminocephalosporanic acid (hereinafter referred to briefly as 7-ACA), or 7-aminodesacetoxycephalosporanic acid (hereinafter referred to briefly as 7-ADCA), when an amino group is introduced] or salts thereof, or acetone adducts thereof, and methods for producing them.

Although it is known that α-aminobenzyl-penicillin andcephalosporin show a broad spectrum of antibacterial activity against both gram-positive and-negative bacteria, it is also well known that they have not sufficient activity against *Escherichia coli* etc. The present inventors studied and investigated this insufficiency and have found that the compounds (I) not only have a broad spectrum of antibacterial action equal to α-aminobenzylderivatives, but also have extremely strong action against *Escherichia coli*. The present invention was accomplished on the basis of these findings.

The principal object of the present invention is to provide novel and useful antibacterial compounds (I).

Another object of the present invention is to provide acetone adducts of the compounds (I), which have prolonged activity.

A further object is to provide 1-cyclohexenylglycine which is employable as an intermediate of the compounds (I).

A still further object is to provide processes for preparing the compounds (I), or salts thereof, or acetone adducts thereof and 1-cyclohexenylglycine.

Other objects of the present invention and advantages thereof will become apparent as the description proceeds.

In the general formula (I) above mentioned, A is a group which forms 6-APA, 7-ACA or 7-ADCA when an amino group is introduced or salts thereof.

These compounds (I) may form corresponding salts with, for example, alkali metals or alkaline earth metals such as sodium, potassium, calcium or aluminum, or organic amines such as trimethylamine, triethylamine, tributylamine, pyridine or the like. The compounds (I) may further be changed to acetone adducts represented by the general formula:

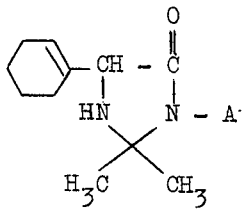

wherein the symbol A has the same meaning as above.

The compounds (I) or salts thereof can, for example, be produced by reacting 1-cyclohexenylglycine or its reactive derivatives with 6-APA, 7-ACA or 7-ADCA.

In this case, each of said 6-APA, 7-ACA or 7-ADCA may be employed as suitable salts thereof or easily hydrolyzable esters thereof, and, when easily hydrolyzable esters are employed, the reaction products are subjected to hydrolysis to obtain the object compounds (I) or salts thereof, if necessary.

In this acylation process, 1-cyclohexenylglycine is usually employed as one of its reactive derivatives, for example, the acid halides such as acid chlorides, acid bromides, etc.; acid azides; acid anhydrides; the mixed alkylphosphoric or alkylcarbonic acid anhydrides; active esters, e.g. corresponding esters with 4-substituted-2,5-oxazolidinedione, pentachlorophenol, N-hydroxysuccinimide, etc.; and the like. If necessary, such condensing agents as cyclohexylcarbodiimide, phosphoryl chloride, N,N'-carbonyl-bis-imidazole, etc. may be employed. The amino group of 1-cyclohexenylglycine is preferably to be protected with, for example with hydrochloric acid, an organic aldehyde, o-nitrothiophenyl, a β-diketone compound (e.g. acetylacetone or acetoacetic ester), azide, or with a group such as carbobenzoxy, p-toluenesulfonyl, phenylthiocarbonyl, aryloxy or phthalyl, isobornyloxycarbonyl, β-methylsulfonylethoxycarbonyl.

6-APA, 7-ACA or 7-ADCA may be used as the corresponding easily hydrolyzable ester with a sililating agent such as trimethylchlorosilane, trimethoxychlorosilane and the like or a silenating agent such as dimethyldichlorosilane, dimethoxydichlorosilane, a tin agent such as tri-n-butyl tin oxide, triphenylchloride, bis-(p-methoxyphenyl) methylchloride, methoxymethylchloride, β-methylthioethylchloride, etc.

These reactions may be carried out in a solvent. However, when an easily hydrolyzable ester is employed, care should be exercised to guard against the entry of moisture into the reaction system. Among the useful solvents are water, alcohols such as ethanol, methanol, etc., acetone, dioxane, tetrahydrofuran, triethylamine, halogenated hydrocarbons such as chlorobenzene, chloroform, methylene chloride, etc., and other organic solvents such as ethyl acetate, ether, acetonitrile and the like. While the reaction temperature is virtually optional, the reaction is often carried out under cooling or at room temperature.

When the reaction according to this invention gives rises to an acid as by-product, a basic reagent such as an alkali, e.g. alkali hydrogen carbonate, alkali carbonate or alkali hydroxide, or an organic amine, e.g. triethylamine or pyridine, is desirably present in the reaction system. In the case of an easily hydrolyzable ester, the product is hydrolyzed in the routine manner and, then, separated by techniques which are conventional per se., e.g. concentration, phasic transfer, chromatography, etc. If necessary, the product may be purified by, for example, recrystallization.

It is to be understood that isomeric forms of the compounds (I) as well as their mixture are included in the scope of the present invention.

Thus-obtained compounds (I) may be led to their acetone adducts, which show more prolonged activity relative to the original compounds (I), by the reaction with acetone.

In this reaction, the volume of acetone is preferably more than one mole relative to the cyclohexenylglycinamide derivatives (I). This reaction generally proceeds readily in a solvent such as, for example, methylene chloride, dimethylformamide, water, chloroform or acetone. The pH of the reaction mixture is preferably maintained within the range of 5.5 to 9.5, and may be controlled with an inorganic alkali, e.g. sodium hydroxide, sodium carbonate, potassium hydroxide or potassium carbonate, an organic amine, e.g. triethylamine, or an acid, e.g. hydrochloric acid or phosphoric acid. The reaction is carried out at room temperature or under heating.

1-Cyclohexenylglycine used as the starting material may be produced by employing per se known methods, for example, by reacting 1-cyclohexene-1-aldehyde with alkali cyanide and an ammonia supplying material, followed by hydrolyzing.

The reaction may be desirably carried out in a hydrophilic solvent such as water, alcohols (e.g. methyl alcohol, ethyl alcohol) or mixture thereof. The reaction may generally at 0°–80°C, preferably be conducted at the temperature ranging from 30° to 40°C.

Alkali cyanide (e.g. sodium cyanide, potassium cyanide) and an ammonia supplying material (e.g. ammonium chloride, ammonium carbonate) may generally be employed from 1 to 1.5 mol respectively relative to 1 mol of the 1-cyclohexene-1-aldehyde.

The reaction is generally completed in a period of from 1 to 4 hours. When ammonium chloride is used as the ammonia supplying material, there is produced an aminonitrile compound, while a hydantoin compound is obtained when ammonium carbonate is employed. While the aminonitrile compound or the hydantoin compound may be isolated, it may be subjected to hydrolysis without isolation. The hydrolysis may be generally conducted by treating the above reaction product with e.g., hydrochloric acid, sulfuric acid, sodium hydroxide, potassium hydroxide or barium hydroxide. When an aminonitrile compound is produced, the hydrolysis is desirably conducted in acid conditions, generally by the use of about 3–12N acid. The reaction is desirably carried out at about room temperature to 100°C. On the other hand, when a hydantoin compound is employed, the reaction is desirably conducted in alkaline conditions and generally at reflux temperature.

The reaction may also be conducted under elevated pressure, if desired. After the completion of the reaction, the reaction mixture may be employed as a starting material without isolation, but may be purified by per se known means such as concentration, phasic transfer, recrystallization, chromatography.

1-Cyclohexenylglycine may also be produced through a 1-cyclohexenyl compound represented by the general formula

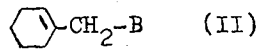

wherein B is a protected or unprotected carboxyl or cyano group. When B represents an unprotected carboxyl group, the subject compound is obtained by subjecting the compound (II) to nitrosation, followed by reduction. When B represents a protected carboxyl or cyano group, the subject compound is obtained by subjecting the compound (II) to nitrosation, then reduction and hydrolysis, in either order.

Among protected carboxyl groups, there are, for example, alkyloxycarbonyl group such as methoxycarbonyl, ethoxycarbonyl, n-(or i-)-propoxycarbonyl, n-(i-,s- or t-)-butoxycarbonyl, n-(or t-) amyloxycarbonyl group, or substituted or unsubstituted phenoxycarbonyl group such as phenoxycarbonyl, p-nitrophenoxycarbonyl, pentachlorophenoxycarbonyl or lower alkoxycarbonyloxycarbonyl group such as t-butoxycarbonyloxycarbonyl, ethoxycarbonyloxycarbonyl, etc.

The nitrosation is conducted by per se known means, for example, reacting 1-cyclohexenyl compound (II) with nitrites or nitrite ester in the presence of an acid (e.g. mineral acid such as hydrochloride, organic carboxylic acid such as acetic acid) or base (e.g. sodium hydride, corresponding alkali metal alcoholate or alkali metal amide with sodium or potassium). Among nitrites, there may be exemplified sodium nitrite, potassium nitrite etc. and, as nitrite ester, there may be alkyl nitrite ester such as methyl nitrite, ethyl nitrite, n-butyl nitrite, t-butyl nitrite, i-amyl nitrite etc.

The reaction is generally carried out at the temperature ranging from 5° to 60°C and proceeds smoothly in a suitable solvent (e.g. alcohols such as methanol, ethanol, aromatic hydrocarbon such as benzene, xylene, halogenated hydrocarbon such as chloroform, carbon tetrachloride, ethers such as ethylether, tetrahydrofuran). The nitrosation reagent may generally be employed from about 1 to 1.2 mol relative to 1 mol of 1-cyclohexenyl compound (II), but is not necessarily limited to this range. The reaction is generally completed in about 0.5 to 2 hours.

Thus obtained 1-cyclohexenyl-α-nitrosoacetic compound is further reduced to convert its α-nitroso group to an amino group.

For this purpose, it was found that per se known reducing means for converting nitroso group to amino group can be employed for the above reduction without acting upon the double bond of the 1-cyclohexenyl group. Among such means, there are, for example, means employing metals (e.g. iron, tin, zinc) or stannous chloride or the like in the presence of an acid (e.g. hydrochloric acid), employing amalgam such as Aluminium amalgam, employing hydrogen sulfide, a salt thereof (e.g. sodium sulfide or polysulfide) in acid, neutral or alkaline conditions. These reactions may be carried out in a solvent such as glacial acetic acid, alcohols such as methanol, ethanol, etc.

Thus-obtained compounds, when B represents a protected carboxyl or cyano group, are subjected to hydrolysis to obtain 1-cyclohexenylglycine. The hydrolysis may be conducted by per se established means, for example by treating compound (II) with a mineral acid such as hydrochloric acid, sulfuric acid, an inorganic base such as sodium hydroxide, potassium carbonate, etc.

These acids or bases are generally used in the concentration from 3 to 6N, but are not necessarily limited to this range.

The reaction is generally carried out in an aqueous solution and, by adding alcohols such as methanol, ethanol, it can be conducted in a high concentration of the compound (II). The reaction may be generally carried out at the temperature from 40° to 100°C, and more desirably from 70° to 100°C.

Thus obtained 1-cyclohexenylglycine itself has relatively strong antibacterial action, and, therefore, it can be utilized as a fungicide. Meanwhile, as 1-cyclohexenylglycine has an asymmetric carbon, it is generally obtained as a racemic compound, which can be subjected, if necessary, to optical resolution by per se known means. For example, there are means employing optically active acid such as L-tartaric acid and D-camphorsulfonic acid or optically active base such as cinchonine, or synthesizing an N-acyl compound of 1-cyclohexenyl glycine and hydrolyzing it with an enzyme such as diastase.

The compounds (I) of the present invention and their acetone adducts have strong-inhibitory action against gram-positive and gram-negative bacteria.

They can be readily absorbed from the small intestines by oral administration, and, in parenteral administration, and they are rapidly penetrated into tissues and have good affinity to tissues. Therefore, the compounds (I) of the present invention are useful as antibacterial agents.

For this purpose, the compounds (I) including their pharmaceutically acceptable acid salts (e.g. sodium, potassium salts) as well as acetone adducts thereof may be orally or parenterally administered per se or in a suitable form such as powder, granules, tablets or injectable solution admixed with a pharmaceutically acceptable carriers, diluents or adjuvants. The present compounds (I), salts thereof or acetone adducts thereof, can be used against almost the same disease that can be cured by α-aminobenzylpenicillin or cephalosporins, as well as the diseases caused by *Escherichia coli*, or the like.

While the dose of the compounds (I) or their acetone adduct to be administered varies depending on the kinds of the compounds, the severity of the disease etc., it generally falls within the range from about 5 to 500 mg./Kg./day for human adult, preferably about 10 to 200 mg/Kg/day for human adult.

It is to be understood that the following examples are solely for the purpose of illustration and not to be construed as limitative of this invention, and that many variations may be resorted to without departing from the spirit and scope of this invention.

In this specification, "part" means "weight part" unless otherwise specified, and the relationship between "part(s) by weight" and "part(s) by volume" corresponds to that of gram(s) and milliliter(s).

EXAMPLE 1

A reactor wherein the air is replaced with dry nitrogen is charged with 250 parts by volume of t-butyl alcohol and then with 12 parts of metallic potassium.

The mixture is vigorously stirred under refluxing in the atmosphere of dry nitrogen to render it completely in the state of solution. Then 100 parts by volume of dry benzene is added to the solution, and the mixture is cooled to 5°C, followed by adding at the same temperature 33.6 parts of ethyl 1-cyclohexenylacetate, and then 35.2 parts of isoamyl nitrite over 30 minutes. The reaction mixture is left standing so that the temperature thereof rises up to the room temperature, and then further stirred for one hour at room temperature.

The reaction mixture is diluted with 200 parts by volume of alcohol, and to the resultant mixture is added 78 parts of zinc powder and then added dropwise 250 parts by volume of concentrated hydrochloric acid under stirring keeping the temperature lower than 30°C by ice-cooling.

The reaction mixture is subjected to filtration, and the insolubles filtered are washed with alcohol. The washing is combined with the filtrate and the mixture is concentrated under reduced pressure, followed by adding about 150 parts of sodium hydrogen carbonate to separate an oily substance. The oily substance is extracted with ether, and the ether is distilled off. To the residue are added 130 parts by volume of 10% aqueous solution of sodium hydroxide and the same volume of ethyl alcohol as the aqueous solution of sodium hydroxide, followed by concentration at 70°C. After two hours, the reaction mixture is filtered to remove insoluble substance, and the filtrate is adjusted to about pH 5.0 with concentrated hydrochloric acid, whereupon 1-cyclohexenylglycine precipitated as crystals. After cooling, the crystals are collected, and washed with water, alcohol and ether, successively, followed by drying to give 16 parts of 1-cyclohexenylglycine melting at 241°C (decomp.).

Elementary analysis Calcd. for $C_8H_{13}NO_2$: C 61.91, H 8.44, N 9.03 Found: C 61.66, H 8.49, N 8.86.

Infrared absorption spectrum (KBr, $cm^{-1}$) 3160. 2600, 1600, 1490, 1400, 1341, 1143, 1108, 718.

1-Cyclohexenylglycine is also obtained in the same manner as above except employing 1-cyclohexenylglycineethoxycarbonate anhydride instead of ethyl 1-cyclohexenylacetate.

EXAMPLE 2

To a cooled solution of 12 parts of metallic potassium in 350 parts by volume of t-butanol, 24.2 parts of 1-cyclohexenylacetonitrile is added under nitrogen current, and then 35.2 parts of isoamyl nitrite at 30°C, followed by stirring for two hours. The reaction mixture is poured into ice-water and shaken with 300 parts by volume of ether. After being separated and washed with ether, the aqueous layer is acidifyed with 19 parts by volume of acetic acid to separate an oily substance. The oily substance is extracted with ether and the extract is washed with a saturated aqueous solution of sodium chloride. After drying, the ether layer is concentrated to give crystals of 1-cyclohexenyl-α-nitrosoacetonitrile.

Aluminium amalgam prepared from 10 parts of aluminium strips is covered with 200 parts by volume of 10 percent ether solution of methyl alcohol and thereto is added portion-wise 100 parts by volume of ether solution of the above-obtained α-nitroso compound. The resultant mixture is permitted to stand overnight. After removing the unreacted metal from the reaction mixture, the filtrate is extracted with 6N-hydrochloric acid. The extract is refluxed for 2 hours and then concentrated so as to give one third of its original volume under reduced pressure.

The concentrate is neutralized with alkali to separate crystals. After being washed with ethyl alcohol, with ether and then water, successively, the crystals are dissolved in 1N-aqueous solution of sodium hydroxide, and then the solution is adjusted to pH of isoelectric point of 1-cyclohexenylglycine with 1N-hydrochloric acid, whereby 9.5 parts of 1-cyclohexenylglycine melting at 241°C (decomp.) is obtained.

The resultant product is identified as the same product obtained in Example 1.

EXAMPLE 3

1.5 Parts of 1-cyclohexenyl-α-nitrosoacetonitrile obtained in Example 2 is dissolved in 20 parts by volume of ethyl alcohol and to the solution is added 10 parts of zinc powder. The mixture is cooled to 5°C to which is added dropwise 10 parts by volume of concentrated hydrochloric acid keeping the internal temperature at 10°C under vigorous stirring, followed by stirring for 30 minutes at room temperature.

Insolubles are removed by filtration from the reaction mixture, which are washed with ether. The filtrate is combined with the washing, and the mixture solution is concentrated under reduced pressure. To the concentrate is added 10 parts by volume of concentrated hydrochloric acid, and the mixture solution is refluxed for 1.5 hours, followed by adjusting its pH to 5.0 with aqueous ammonia, whereby 0.7 part of 1-cyclohexenylglycine is obtained.

EXAMPLE 4

After 13.8 parts of metallic sodium is dissolved in 200 volume parts of methyl alcohol under nitrogen current, the methyl alcohol is distilled off. The residue is suspended in 200 volume parts of dry benzene. The solution is cooled down to a temperature of 0°C–5°C. To the solution is added 48.4 parts of 1-cyclohexenylacetonitrile under vigorous stirring followed by the addition of 70.4 parts of isoamyl nitrite at the same temperature. The solution is stirred at 10°C for one hour, whereby sodium salt of nitroso compound separates out. The salt is dissolved in 200 volume parts of water. The solution is extracted with benzene. The benzene layer is further extracted twice with 200 volume parts of water. The aqueous layers are combined, and shaken with 200 volume parts of ether. The aqueous layer is separated, and added dropwise over 2 hours under vigorous stirring to a boiling aqueous solution of 60 parts of sodium hydroxide in 200 volume parts water. Thereafter, the reaction solution is stirred for 3 hours, while removing then generated ammonia by distillation. The remaining solution is neutralized with 170 volume parts of concentrated hydrochloric acid to give α-nitroso-1-cyclohexenylacetic acid as crystals melting at 136°C to 137°C.

The precipitates are mixed with 104 parts of zinc powder. To the resulting mixture is added under vigorous stirring at a temperature not higher than 30°C dropwise 320 volume parts of concentrated hydrochloric acid, followed by further stirring for 30 minutes. Unreacted zinc is filtrated off. The filtrate is concentrated to one half of its original volume.

The concentrate is adjusted to pH 6 with an aqueous solution of sodium hydroxide, and then the precipitating crude crystals are collected and washed. The crystals are dissolved in 1N-aqueous solution of sodium hydroxide. Then, pH of the solution is adjusted to about 5 with hydrochloric acid, whereby 1-cyclohexenylglycine is obtained as crystals melting at 241°C which is found to be identified as the same product obtained in Example 1. 1-Cyclohexenylglycine can be converted to 1-cyclohexenylglycine chloride hydrochloride by a similar manner to that disclosed in J.C.C. 31 (1966) 898.

EXAMPLE 5

A solution of 4.4 parts of 1-cyclohexene-1-aldehyde in 8 parts by volume of methanol is added to a solution of 2 parts of sodium cyanide and 2.36 parts of ammonium chloride in 8 parts by volume of water and the mixture is stirred at room temperature for 2 hours, at the end of which time 20 parts by volume of water is added. The resulting aminonitrile compound is extracted with 20 parts by volume of benzene. The benzene layer is extracted three times with 10 parts by volume portions of 6N-hydrochloric acid, respectively, and the aqueous layer is refluxed for 2 hours. The resinous matter is removed with activated carbon and the filtrate is concentrated to about 15 parts by volume and brought to about pH 5.0 with concentrated aqueous ammonia (28%), whereupon crude crystals of DL-1-cyclohexenylglycine is separated out. The crystals are recovered by filtration and dissolved in 1N-aqueous solution of sodium hydroxide. To the solution is added activated carbon and the mixture is subjected to filtration. To the filtrate, ethanol (one-half volume of the filtrate) is added, and the mixture is boiled, followed by adjusting its pH to about 5.0 with hydrochloric acid, whereby 1.1 parts of DL-1-cyclohexenylglycine as colorless flakes melting at 242°–243°C is obtained.

IR(KBr, cm$^{-1}$) 3160, 2960, 1605, 1490, 1400, 1345, 1274, 1145, 720.

NMR (solvent: 1N-NaOD) 1.5 – 2.4 (multiplet, 8H) 3.81 (singlet, 1H, — C$\underline{H}$ — COOH) 5.84 (multiplet, 1H, — C$\underline{H}$ = C —)

EXAMPLE 6

To a solution of 13 parts of potassium cyanide are added 11 parts of 1-cyclohexene-1-aldehyde, 38.4 parts of ammonium carbonate and 100 parts by volume of ethyl alcohol (50%) and the mixture is stirred at 60°–65°C for 2 hours, at the end of which time the ethyl alcohol is distilled off under reduced pressure. The residue is acidified with dilute hydrochloric acid to precipitate crystals. 5 Parts of the crystals are hydrolyzed to give 2.7 parts of 1-cyclohexenylglycine. The mixed examinations of this substance with the product obtained in Example 1 does not show any depression of the melting point.

EXAMPLE 7

1. 5 Parts of 1-cyclohexenylglycine is dissolved in 33.2 parts by volume of 1N-aqueous solution of sodium hydroxide. To the solution are added alternatively 1N aqueous solution of sodium hydroxide and chloroacetylchloride keeping the pH alkaline under ice-cooling, so that the total quantity of the former may reach 39.2 parts by volume and that of the latter may reach 4.2 parts by volume. The reaction mixture is left standing and its temperature rises up to the room temperature. It is then stirred for 2 hours at the same temperature. After being adjusted to pH 8.0, the resulting mixture is shaken with ether. The aqueous layer is adjusted to pH 2.5 with 2N-hydrochloric acid and the resulting suspension is extracted with ether three times. The combined ether extract is washed twice with saturated aqueous solution of sodium chloride, followed by drying.

The ether solution is subjected to distillation to give crystals which are recrystallized from benzene-ether, whereby 4.5 parts by volume of N-chloroacetyl-1-cyclohexenylglycine melting at 137°–140°C is obtained.

Elementary analysis: Calcd. for $C_{10}H_{14}NO_3Cl$: C 51.84, H 6.09, N 6.04, Cl 15.30, Found: C 51.78, H 5.86, N 5.83, Cl 15.52.

IR (KBr cm$^{-1}$) 3360, 2650, 1730, 1625, 1545, 1410, 1255, 1210, 1155, 1010, 885, 785.

2. One part of thus obtained N-chloroacetyl-1-cyclohexenylglycine is suspended in 25 parts by volume of water and to the suspension is added 4.5 parts by volume of 1N-aqueous solution of sodium hydroxide to obtain a homogeneous solution. To the solution is added a solution of 5 parts of diastase dissolved in 40 parts by volume of water, and the solution is adjusted to pH 7.2 with a 1N-aqueous solution of sodium hydroxide, followed by stirring for 115 hours at 37°C. The reaction mixture is subjected to filtration to remove the sediments and the filtrate is adjusted to pH 2.5 with 2N-hydrochloric acid, followed by extraction with ethyl acetate.

The ethyl acetate extract is washed with a saturated solution of sodium chloride, dried and concentrated to separate crystals. Recrystallization from ethyl acetate three times gives 0.2 part of D(−)-N-chloroacetyl-1-cyclohexenylglycine melting at 137°–138°C as colourless powdery crystals.

$[\alpha]_D = -136°$ (EtOH C=1.0%)

Elementary analysis: Calcd. for $C_{10}H_{14}NO_3Cl$: C 51.84, H 6.09, N 6.04, Cl 15.30, Found: C 52.03, H 5.71, N 5.97, Cl 15.30.

3. A suspension of 0.1 part of D(−)-N-chloroacetyl-1-cyclohexenylglycine in 4 parts by volume of 6N-hydrochloric acid is refluxed for 15 minutes. The reaction mixture is concentrated to about one part by volume, and then the pH of the concentrate is adjusted to 5.0 with 7N-aqueous ammonia to separate crystals. The crystals are washed with cold water and dried to give 0.03 part of D(−)-1-cyclohexenylglycine melting at 224°–225°C.

$[\alpha]_D = -147.7$ (1N-HCl, C=1.0%)

4. The aqueous layer obtained above in (2) is adjusted to pH 5.0 with a 1N-aqueous solution of sodium hydroxide and concentrated under reduced pressure. The concentrated solution is adsorbed on 20 parts by volume of Amberlite IR-120B (manufactured by Rohm & Haas Co., U.S.A.).

The resin is collected by filtration and washed with 500 parts by volume of water, followed by extraction with 1.5N aqueous ammonia.

The extract is concentrated to separate crystals, whereby 0.15 part of L(+)-1-cyclohexenylglycine is obtained.

$[\alpha]_D = +147°$ (1N—HCl, C=1.0%)

EXAMPLE 8

A solution of 0.63 part of sodium 1-cyclohexenylglycinate and 0.42 part of methyl acetoacetate in 40 parts by volume of methanol is stirred at 60°C for 3 hours. The reaction solution is concentrated and the resulting enamine compound is dried well and dissolved in 25 parts by volume of dry chloroform. The solution is cooled to −20°C, and a solution of 0.49 part of isobutyl chlorocarbonate in 10 parts by volume of chloroform is added thereto over 5 minutes. The mixture is stirred at a temperature ranging from −20°C to −8°C for 2 hours. Then, at −10°C, a solution containing 0.78 part of 6-aminopenicillanic acid, 0.4 part of triethylamine and 30 parts by volume of chloroform is added, followed by stirring at −5° to 5°C for 2 hours. The reaction mixture is concentrated and the residue is dissolved in a solution of 0.75 part of sodium hydrogen carbonate in 50 parts by volume of water. After washing with ether, the aqueous layer is recovered and adjusted to pH 2.5 with 2N-hydrochloric acid. The layer is stirred at room temperature for 30 minutes, and the oily matter separated is shaken twice with ether. The ether layer is discarded and the aqueous layer is adjusted to pH 4.0 with sodium hydrogen carbonate, followed by freeze-drying. The resulting crude product is purified by column chromatography, whereby 0.3 part of 6-[1'-cyclohexenylglycinamido]-penicillanic acid is obtained from a water-ethanol (4:1) eluate.

IR(KBr). 3400 cm⁻¹, 3350 cm⁻¹, 1775 cm⁻¹, 1685 cm⁻¹, 1600 cm⁻¹, 1530 cm⁻¹, 1510 cm⁻¹, 1200 cm⁻¹.

The following shows minimum growth inhibitory concentrations of 6-(1'-cyclohexenylglycinamido)-penicillanic acid.

|  | (γ/ml.) |
|---|---|
| *Staphylococcus aureus* 209P | < 0.2 |
| *Bacillus subtilis* | < 0.2 |
| *Sarcina lutea* | < 0.2 |
| *Escherichia coli* | 0.5 |
| *Proteus morganii* Eb54 | 1 |

EXAMPLE 9

A reactor, wherein the air is replaced with nitrogen is charged with 5.2 parts of dry 6-aminopenicillanic acid and 51 parts by volume of dry methylene chloride, followed by thorough stirring. To the mixture, there are added 7.3 parts by volume of triethylamine and 3.4 parts by volume of N,N-dimethylaniline. Then, 6.9 parts by volume of trimethylchlorosilane is added dropwise to the mixture at a temperature of 0° to 5°C and the reaction mixture is stirred at 10°C for 30 minutes. Then, the reaction mixture is allowed to warm and, at room temperature, stirred for 2.5 hours. To this reaction mixture is added 5.05 parts of 1-cyclohexenylglycine chloride hydrochloride at a temperature of 0°–5°C, followed by stirring at 0°–10°C for 30 minutes, at 10°–15°C for 1.5 hours and at 15°–17°C for 1.5 hour.

The reaction mixture is poured into 144 parts by volume of cold water and stirred at a temperature of 0°–5°C for 30 minutes. After the addition of 0.7 part of Celite, the mixture is filtered and washed with cold water. The filtrate is combined with the washing and the aqueous layer is separated and washed with ethyl acetate. The aqueous layer is separated and adjusted to pH 4.0 with sodium bicarbonate, whereby 6-(1'-cyclohexenylglycinamido)penicillanic acid is obtained as white precipitates.

EXAMPLE 10

A solution of 0.51 part of sodium D(−)-1-cyclohexenylglycine and 0.37 part of methyl acetoacetate in 30 parts by volume of methyl alcohol is stirred at 60°C for 2 hours. The reaction solution is concentrated to give an enamine compound. After drying well, the enamine compound is dissolved in 25 parts by volume of dry chloroform. To the solution is added a solution of 0.5 part of isobutyl chlorocarbonate in 10 parts by volume of chloroform at −20°C, followed by stirring for 2 hours at a temperature ranging from −15°C to −8°C.

To the reaction mixture is added a solution of 0.63 part of 6-aminopenicillanic acid, 0.3 part of triethylamine in 30 parts by volume of chloroform at the same temperature, as above, followed by stirring for 2 hours at a temperature ranging from −2°C to 5°C.

The reaction mixture is subjected to concentration and the residue is dissolved in a solution of 1 part of sodium hydrogen carbonate in 100 parts by volume of water. The solution is adjusted to pH 2.6 with 2N-hydrochloric acid and stirred for 30 minutes.

The reaction mixture is shaken with ether and the aqueous layer is adjusted to pH 4.0, followed by purifing with chromatography to obtain 0.2 part of 6-[D(−)-α-amino-1′-cyclohexenyl-acetoamido]penicillanic acid.

$[\alpha]_D = +225.2°$ (1N-HCl, C=0.55%)

IR(KBr cm$^{-1}$); 1780, 1690, 1605, 1510, 1390, 1310, 1245, 1127.

Rf value; 0.6 (solvent; n-butyl alcohol : acetic acid : water = 3 : 1 : 1)

EXAMPLE 11

A reactor, wherein the air is replaced with nitrogen, is charged with 5.2 parts of dry 6-aminopenicillanic acid and 51 parts by volume of dry methylene chloride, 6.8 parts by volume of triethylamine and 3.36 parts by volume of N,N-dimethylaniline, followed by stirring. To the mixture is added 3.1 parts of dimethyldichlorosilane dropwise at a temperature of 10° to 15°C over 20 minutes. Then, the reaction mixture is allowed to warm and is stirred at 25°C for 1.5 hours. To the resultant solution is added 5.05 parts of 1-cyclohexenylglycyl chloride hydrochloride at a temperature of 0° to 5°C over 45 minutes, followed by stirring at 0° to 5°C for 15 minutes, at 5°–10°C for 1.5 hours and at 10° C for 1.5 hours. The reaction mixture is poured into 144 parts by volume of cold water and the mixture is stirred at a temperature of 5°–10°C for 15 minutes. The reaction mixture is subjected to filtration with the addition of 0.7 part Celite.

The filter cake is washed with cold water and the washings are combined with the filtrate obtained above. To the aqueous layer is added 20 parts by volume of ethyl acetate, and to the mixture is added dropwise a solution of 5.62 parts by volume of diphenylsulfonic acid in 15 parts by volume of water, at a temperature of 0°–5°C while adjusting its pH to 1.5 with an 5N-aqueous solution of sodium hydroxide whereby diphenylsulfonate of 6-(1-cyclohexenylglycinamido)-penicillanic acid precipitates out.

After being stirred for 6 hours at 5°C, the reaction mixture is filtered and the filter cake is washed with 30 parts by volume of cold water of pH 1.5 to 2.0 and with 30 parts by volume of ethyl acetate. The filter cake is further washed twice with 6 parts by volume each of ethyl acetate, followed by subjecting the filter cake to thorough sucking to give 15 parts of diphenylsulfonate of 6-(1-cyclohexenylglycinamido)-penicillanic acid. The salt is suspended in 17 parts by volume of 85% of isopropyl alcohol and to the mixture is added 17 parts by volume of triethylamine followed by stirring for 45 minutes at a temperature of 60°–70°C, whereby precipitates are formed. The precipitates are collected by filtration under heating, and washed thrice with 5 parts by volume each of 85% of isopropyl alcohol, followed by drying over phosphorus pentoxide under reduced pressure to give 2.0 parts of 6-(1-cyclohexenyl-glycinamido)-penicillanic acid anhydride as white powder. This product shows characteristic IR absorptions at 3340 cm$^{-1}$(—NH—), 1760 cm$^{-1}$ (β-lactam carbonyl), 1690 cm$^{-1}$ (amido carbonyl), 1600 cm$^{-1}$ (carboxylate) and 1510 cm$^{-1}$ (amide).

The minimum growth inhibitory concentration is 0.2 μg/ml against staphylococcus pyogenes var. aureus and 0.8 μg/ml against *Escherichia coli*.

EXAMPLE 12

A reactor, wherein the air is replaced with nitrogen is charged with 5.2 parts dry 6-aminopenicillanic acid and, then, 51 parts by volume dry methylene chloride. Then, 6.8 parts by volume triethylamine and 3.36 parts by volume N,N-dimethylaniline are added, and the mixture is stirred, followed by the dropwise addition of 3.1 parts of dimethyldichlorosilane at a temperature of 10°–15°C over 20 minutes. This reaction mixture is allowed to warm and, at 25°C, stirred for 1.5 hour. To the thus-obtained solution is added 5.05 parts of 1-cyclohexenylglycine chloride hydrochloride at a temperature of 0°–5°C over 45 minutes. The mixture is stirred at 0°–5°C for 15 minutes, at 5°–10°C for 1.5 hours and at 10°C for 1.5 hours. This reaction mixture is poured into 144 parts by volume of cold water, followed by stirring at 5°–10°C for 15 minutes. After the addition of 0.7 part Celite, the mixture is filtered. The filter cake is washed with cold water and the filtrate is combined with the washings. The aqueous layer is washed with ethyl acetate. At a temperature 0°–5°C, the aqueous layer is adjusted to pH 4.0 with sodium bicarbonate, whereby the 6-(1′-cyclohexenylglycinamido)-penicillanic acid is obtained as white precipitates.

EXAMPLE 13

In 20 parts by volume of methanol is dissolved 0.72 part of sodium 1-cyclohexenylglycinate and to the solution is added 0.47 part of methyl acetoacetate. The mixture is stirred at 50°C for 2 hours, followed by concentration to dryness. Thus-obtained enamine compound is directly dissolved in 25 parts by volume of chloroform and, at −15°C, a solution of 0.55 part of isobutyl chlorocarbonate in 10 parts by volume of chloroform is added. The mixture is stirred at −8°C for 90 minutes.

Then, a solution of 1.08 part of 7-aminocephalosporanic acid and 0.41 part of triethylamine in 30 parts by volume of chloroform is added dropwise at −5°C over 10 minutes, followed by stirring at a temperature of 0°–5°C for 2 hours. The mixture is concentrated and the residue is dissolved in 100 parts by volume of a 1% aqueous solution of sodium hydrogen carbonate. After the solution is adjusted to pH 2.5 with 2N-hydrochloric acid and stirred for 30 minutes, it is shaken with ether. The aqueous layer is adjusted to pH 3.8 with Sodium hydrogen carbonate followed by concentration to give 7-(1′-cyclohexenylglycinamido)-cephalosporanic acid.

EXAMPLE 14

In a mixture of 20 parts by volume of ethyl acetate and 1.64 parts of triethylamine, 2.16 parts of 7-aminocephalosporanic acid is suspended and, 0.87 part of trimethylsilyl chloride is added to the suspension at a temperature of 0°–10°C. The temperature is gradually heightened and, at room temperature, the mixture is further stirred for 3 hours.

Then, under cooling with ice, 1.05 parts of quinoline is added to the reaction mixture, followed by the addition of a solution of 1.68 parts of 1-cyclohexenylglycine chloride in 20 parts by volume of ethyl acetate. The mixture is stirred at room temperature for 3 hours.

The reaction mixture is concentrated and, then, dissolved in 160 parts by volume of 1% aqueous solution of sodium hydrogen carbonate. The solution is washed with ether, and the aqueous layer is adjusted to pH 3.8 with 2N-hydrochloric acid, followed by concentration. The concentrate is purified by column chromatography to give 7-(1'-cyclohexenylglycinamido)-cephalosporanic acid.

Melting point: 195°–200°C (decomp.).

Rf value: 0.25 (n-BuOH : $H_2O$ : tetrahydrofuran = 3 : 1 : 1); 0.57 (n-BuOH : $H_2O$ : acetic acid = 3 : 1 : 1)

Elementary analysis: Calculated for $C_{18}H_{23}N_3SO_6 \cdot H_2O$, C 50.57, H 5.89, N 9.82, S 7.50; Found: C 50.24, H 5.74, N 9.83, S 7.54.

Ultraviolet absorption spectrum; (in $H_2O$) 258 mμ ($\epsilon$=7.737).

EXAMPLE 15

In 40 parts by volume of ethyl alcohol is suspended 1.8 parts of sodium 1-cyclohexenylglycinate, and 1.45 parts of ethyl acetoacetate is added thereto. The mixture is refluxed for 3 hours at 65°C, and the reaction mixture is subjected to distillation of ethyl alcohol, followed by drying. The residue (enamine compound) is dissolved in 50 parts by volume of chloroform and, to the solution, 1.36 parts by volume of isobutyl chlorocarbonate dissolved in 10 parts by volume of chloroform is added at a temperature from −15° to −10°C, followed by stirring for two hours at the same temperature.

To the resultant mixture is added dropwise a solution of 2.14 parts of 3-desacetoxy-7-aminocephalosporanic acid and 1.1 parts of triethylamine dissolved in 100 parts by volume of chloroform at −5°C, followed by stirring for 2 hours at a temperature from −5° to 0°C.

The reaction mixture is subjected to concentration and the residue is dissolved in an aqueous solution of 2 parts of sodium hydrogen carbonate in 100 parts by volume of water, followed by extraction with ethyl acetate. The aqueous layer is adjusted to pH 2.5 with 2N-hydrochloric acid and stirred for 30 minutes. The aqueous solution is shaken with ethyl acetate, and the aqueous layer is adjusted to pH 4.5, followed by concentration. The concentrate is purified by chromatography to give 3-desacetoxy-7-(1'-cyclohexenylglycinamido)-cephalosporanic acid.

EXAMPLE 16

In 25 parts by volume of dry methylene chloride is suspended 1.1 parts of 7-aminodesacetoxycephalosporanic acid. Then, 1.1 parts of dry triethylamine is added to the above suspension, followed by the addition of 0.63 part of N,N-dimethylaniline. The mixture is stirred well, and under cooling with ice-water, 0.65 part of dimethyldichlorosilane is added thereto dropwise at 10°C.

The mixture is stirred at room temperature for 2 hours. To the mixture is added portionwise 1.1 parts of powdered D(−)1-cyclohexenylglycine chloride hydrochloride at a temperature lower than 10°C. The mixture is stirred at 10°C for 1.0 hour, at 10°–15°C for 1.5 hours and at 15°–17°C for 1.5 hours. Then, the reaction mixture is poured into 30 parts by volume of ice-water. The pH of the solution is adjusted to 1.3. The solution is stirred for 15 hours and then 1.0 part of Celite is added. The mixture is stirred for another 10 minutes, followed by filtration. The filtrate is brought to pH 4.7 with 1N-KOH and freeze-dried to give 3.0 parts of pale-yellowish powder. The powder is subjected to thin-layer chromatography using a solvent system of acetic acid : n-BuOH : $H_2O$ (1 : 3 : 1). It is found that this product is a mixture of 4 different compounds.

To 20 parts by volume of water, is added 2.0 parts of the said powder, followed by the addition of 1N-aqeous solution of potassium hydroxide to bring the pH to 6.9. The resulting solution is purified by the use of an Amberlite XAD II column (manufactured by Rohm & Haas Co., U.S.A.) and the portion obtained with 10% ethyl alcohol (positive in ninhydrin and palladium chloride reactions) is freeze-dried, whereupon 0.85 part of 7-(D(−)1'-cyclohexenylglycinamido) desacetoxycephalosporanic acid is obtained as white feather-like crystals. This product shows characteristic infrared absorption spectrum at 1770 $cm^{-1}$, 1690 $cm^{-1}$, 1600 $cm^{-1}$ (broad) and 1520 $cm^{-1}$.

EXAMPLE 17

A mixed solution of 6.0 parts of 6-(1'-cyclohexenylglycinamido) penicillanic acid, 1.1 parts of water, 4.9 parts by volume of triethylamine and 35 parts by volume of acetone is stirred at room temperature for 16 hours. The resulting reaction mixture is poured into 50 parts by volume of ice-water and, simultaneously, 2N-hydrochloric acid is added. Under cooling with ice, the mixture is stirred in a pH range of 2.5 to 3.0 for 2 hours. The precipitate is washed with cold hydrochloric acid (pH 2.5) and dried in a vacuum desiccator over phosphorus pentoxide, whereupon 6-[2',2'-dimethyl-4'-(1''-cyclohexenyl)-5'-oxo-1'-imidazolidinyl]penicillanic acid is obtained as white powder. The infrared absorption spectrum of this product shows an absorption corresponding to the β-lactam ring at 1785 $cm^{-1}$ and an absorption corresponding to the γ-lactam ring at 1720 $cm^{-1}$.

Elementary analysis Calcd. for $C_{19}H_{27}N_3O_4S$: C 57.99, H 6.92, N 10.68, S 8.15, Found: C 57.50, H 6.99, N 10.65, S 7.60.

EXAMPLE 18

In 25 parts by volume of acetone is suspended 3.5 parts of 7-(D(−)1-cyclohexenylglycinamido) desacetoxycephalosporanic acid, and, 1.5 parts by volume of triethylamine is added. The mixture is stirred at room temperature for 20 hours, at the end of which time it is filtered. The filtrate is concentrated under reduced pressure and the acetone is removed by distillation. To the residue, there is added 25 parts by volume of ice-water, and under cooling with ice and stirring, the mixture is adjusted to pH 3.0 with 1N-hydrochloric acid, whereupon precipitates are formed. Under cooling with ice, the mixture is stirred for 2 hours and the precipitates are collected by filtration, washed with cold water and, then, with acetone, followed by drying in a vacuum desiccator over phosphorus pentoxide, whereupon 2.4 parts of 7-[2'2'-dimethyl-4'-(D(−)1''-cyclohexenyl)-5'-oxo-1'-imidazolidinyl] desacetoxycephalosporanic acid is obtained as white powder.

This product shows characteristic absorptions in the infrared region of the spectrum at 1785 $cm^{-1}$ (β-lactam carbonyl) and 1700 $cm^{-1}$ (broad) (imidazolidinone ring —CO). The absorption bands of the amide at 1680 and 1520 $cm^{-1}$ are absent.

EXAMPLE 19

In 8 parts by volume of dry dimethylformamide is dissolved 2.0 parts of 7-(D-(−)1'-cyclohexenylglycinamido) cephalosporanic acid, and the solution is admixed with 0.7 part by volume of triethylamine. Then at 10°C, 0.5 part of methylchloromethyl sulfide is added dropwise. The mixture is stirred at room temperature for 4 hours, at the end of which time it is filtered. The filtrate is concentrated under reduced pressure for a while and, then, poured into 400 parts by volume of ice-water. After the mixture is adjusted to pH 7.0 the insolubles are collected by filtration, washed with 2 parts by volume of ice-water and dried in a vacuum desiccator over $P_2O_5$, whereupon crude 7-(D(−)1′-cyclohexenylglycinamido) cephalosporanic acid methylsulfenylmethyl ester is obtained as pale-yellowish powder. The powder is dissolved in 10 parts by volume of acetone and the solution is stirred at room temperature for 16 hours. The acetone is removed by distillation under reduced pressure, and the syrupy residue is added to 20 parts by volume of ice-water, followed by stirring for a while.

Then, the mixture is brought to pH 3.0 with 1N-HCl and the precipitating crystals are collected by filtration, washed with ice-water and dried in a vacuum desiccator over phosphorus pentoxide, whereupon 0.4 part of 7-[2′,2′-dimethyl-4′-(D(−)-1″-cyclohexenyl)-5′-oxo-1′-imidazolidinyl] cephalosporanic acid is obtained as white powder.

What is claimed is:

1. A compound selected from the group consisting of 6-(1′-cyclohexenylglycinamido)penicillanic acid and non-toxic pharmaceutically acceptable salts thereof.

2. The compound according to claim 1, namely 6-(1′-cyclohexenylglycinamido) penicillanic acid.

* * * * *